US005519114A

United States Patent [19]
Johnson et al.

[11] Patent Number: 5,519,114
[45] Date of Patent: May 21, 1996

[54] RETROVIRAL SUPERANTIGENS, SUPERANTIGEN PEPTIDES, AND METHODS OF USE

[75] Inventors: Howard M. Johnson; Barbara A. Torres; Janet K. Yamamoto, all of Gainesville, Fla.

[73] Assignee: University of Florida Research Foundation, Inc., Gainesville, Fla.

[21] Appl. No.: 145,708

[22] Filed: Oct. 29, 1993

[51] Int. Cl.$^6$ ............... C07K 14/16; A61K 38/16; A61K 39/21; G01N 33/53
[52] U.S. Cl. ............. 530/324; 424/188.1; 424/278.1; 435/5; 530/221
[58] Field of Search .................. 530/324; 514/12; 424/188.1, 278.1; 930/221; 435/5

[56] References Cited

U.S. PATENT DOCUMENTS 5,221,610  6/1993  Montagnier et al. .................. 435/7.1

FOREIGN PATENT DOCUMENTS 2650954  2/1991  France ............... A61K 37/02
8909227  10/1989  WIPO ............... C07K 7/00

OTHER PUBLICATIONS

Cernescu, C. et al. 1992 Rev. Roum. Virol. vol. 43 pp. 95–100.
Sabatier, J. M. et al. 1990 Int. J. Peptide Protein Res. vol. 35 pp. 63–72.
Choppin, J. et al. 1991 J. Immunol. vol. 147 pp. 569–574.
Johnson, H. M. et al. (1988) "Potent Mitogenic Activity of Staphylococcal Enterotoxin A Requires Induction of Interleukin 2" Int. Arch. Allergy Appl. Immunol. 87:87–90.
Carlsson, R. et al. (1988) "Binding of Staphylococcal enterotoxin A to Accessory Cells is a Requirement for its Ability to Activate Human T Cells" J. Immunol. 140:2484–2488.
Fleischer, B. et al. (1988) "T Cell Stimulation by Staphylococcal Enterotoxins" J. Exp. Med. 167:1697–1707.
Mollick, J. A. et al. (1989) "Class II MHC Molecules Are Specific Receptors for Staphylococcus Enterotoxin A" Science 244:817–820.
Janeway, C. A. et al. (1989) "T–Cell Responses to Mls and to Bacterial Proteins that Mimic its Behavior" Immunol. Rev. 107:61–88.
White, J. et al. (1989) "The Vβ–Specific Superantigen Staphylococcal Enterotoxin B: Stimulation of Mature T Cells and Clonal Deletion in Neonatal Mice" Cell 56:27–35.
Herman, A. et al. (1991) "Superantigens: Mechanism of T–Cell Stimulation and Role in Immune Responses" Ann. Rev. Immunol. 9:745–772.
Kawabe, Y. et al. (1991) "Programmed Cell Death and Extrathymic Reduction of Vβ8$^+$ CD4$^+$ T Cells in Mice Tolerant to *Staphylococcus aureus* Enterotoxin B" Nature 349:245–248.
Kawabe, Y. et al. (1990) "Selective Anergy of Vβ8$^+$, CD4 + T Cells in Staphylococcus Enterotoxin B–primed Mice" J. Exp. Med. 172:1065–1070.

Rellahan, B. L. et al. (1990) "In Vivo Induction of Anergy in Peripheral Vβ8$^+$ T Cells by Staphylococcal Enterotoxin B" J. Exp. Med. 172:1092–1100.
Fischer, H. et al. (1990) "Production of TNF–α and TNF–β by Staphylococcal Enterotoxin A Activated Human T Cells" J. Immunol. 144(12):4663–4669.
Gjorloff, A. et al. (1991) "Induction of Interleukin–1 in Human Monocytes by the Superantigen Staphylococcal Enterotoxin A Requires the Participation of T Cells" Cell. Immunol. 137:61–71.
Scholl, P. R. et al. (1992) "Role of Protein Tyrosine Phosphorylation in Monokine Induction by the Staphylococcal Superantigen Toxic Shock Syndrome Toxin–1$^1$" J. Immunol 148(7):2237–2241.
Yokota, S. et al. (1988) "Enhancement of Antigen–and Mitogen–induced Human T Lymphocyte Proliferation by Tumor Necroses Factor–α$^1$" J. Immunol. 140(2):531–536.
Pontzer, C. H. et al. (1989) "Localization of an Immune Functional Site on Staphylococcal Enterotoxin A Using the Synthetic Peptide Approach" J. Immunol. 143(1):280–284.
Pontzer, C. H. et al. (1990) "Site of Nonrestrictive Binding of SEA to Class II MHC Antigens" Int. Arch. Allergy Appl. Immunol. 93:107–112.
Griggs, N. D. et al. (1992) "Mapping of Multiple Binding Domains of the Superantigen Staphlococcal Enterotoxin A for HLA" J. Immunol. 148:2516–2521.
Grossman, D. et al. (1990) "Dissociation of the Stimulatory Activities of Staphylococcal Enterotoxins for T Cells and Monocytes" J. Exp. Med. 172:1831–1841.
Grossman, D. et al. (1990) "Mutation of the Disulfide Loop in Staphylococcaal Enterotoxin A—Consequences for T Cell Recognition" J. Exp. Med. 147(10):3274–3281.
Acha–Orbea, H. et al. (1988) "Limited Heterogeneity of T Cell Receptors from Lymphocytes Mediating Autoimmune Encephalomyelitis Allows Specific Immune Intervention" Cell 54:263–273.
Offner, H. et al. (1991) "T Cell Receptor Peptide Therapy Triggers Autoregulation of Experimental Encephalomyelitis" Science 251:430–432.
Kim, C. et al. (1991) "Reduction of Lupus Nephritis in MRL/1pr Mice by a Bacterial Superantigen Treatment" J. Exp. Med. 174:1431–1437.
Pullen, A. M. et al. (1992) "The Open Reading Frames in the 3' Long Terminal Repeats of Several Mouse Mammary Tumor Virus Integrants Encode V/β3–specific Superantigens" J. Exp. Med. 175:41–47.

(List continued on next page.)

*Primary Examiner*—Mary E. Mosher
*Attorney, Agent, or Firm*—Saliwanchik & Saliwanchik

[57] ABSTRACT

The subject invention concerns novel superantigen proteins and peptides and methods of use of these superantigens. Specifically exemplified are peptide agonists from mouse mammary tumor virus, feline immunodeficiency virus and human immunodeficiency virus. The peptides can also be used to produce, purify and detect antibodies that bind to superantigens. These superantigens and their corresponding peptides can be used in both diagnostic and therapeutic protocols.

1 Claim, 5 Drawing Sheets

OTHER PUBLICATIONS

Choi, Y. et al. (1992) "Structural Analysis of a Mouse Mammary Tumor Virus Superantigen" J. Exp.Med. 175:847–851.

Laurence, J. et al. (1992) "Superantigen Implicated in Dependence of HIV-1 Replication in T Cells on TCR Vβ Expression" Nature 358:255–259.

Gougeon, M. L. et al. (1993) "Apoptosis in AIDS" Science 260:1269–1270.

Kiyomasu, T. et al. (1991) "Identification of Feline Immunodeficiency Virus rev Gene Activity" Journal of Virology 65(8):4539–4542.

Cullen, B. R., ed. (1993) "Molecular Biology of the Human Spumavirus" Human Retroviruses 205–206.

Allan, J. S. et al. (1985) "A New HTLV–III/LAV Encoded Antigen Detected by Antibodies from AIDS Patients" Science 230:810–813.

Laurent, A. G. et al. (1990) "Production of a Non–Functional nef Protein in Human Immunodeficiency Virus Type 1–Infected CEM Cells" J. Gen. Virol. 71:2273–2281.

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Asp Ser Phe Asn Asn Ser Ser Val Gln Asp Tyr Asn Leu Asn Asp Ser
 1               5                  10                  15
Glu Asn Ser Thr Phe Leu Leu Gly Gln Gly Pro Gln Pro Thr Ser Ser
                20                  25                  30
Tyr Lys Pro His Arg Leu Cys Pro Ser Glu Ile Glu
                35                  40
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Glu Ile Glu Ile Arg Met Leu Ala Lys Asn Tyr Ile Phe Thr Asn Glu
 1               5                  10                  15
Thr Asn Pro Ile Gly Arg Leu Leu Ile Met Met Leu Arg Asn Glu
                20                  25                  30
```

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Met Leu Arg Asn Glu Ser Leu Ser Phe Ser Thr Ile Phe Thr Gln
 1               5                  10                  15

Ile Gln Arg Leu Glu Met Gly Ile Glu Asn Arg Lys Arg Arg Ser
            20                  25                  30
```

( 2 ) INFORMATION FOR SEQ ID NO:4:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Glu Asn Arg Lys Arg Arg Ser Thr Ser Val Glu Glu Gln Val Gln Gly
 1               5                  10                  15

Leu Arg Ala Ser Gly Leu Glu Val Lys Arg Gly Lys Arg Ser
            20                  25                  30
```

( 2 ) INFORMATION FOR SEQ ID NO:5:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Lys Arg Gly Lys Arg Ser Ala Leu Val Lys Ile Gly Asp Arg Trp Trp
 1               5                  10                  15

Gln Pro Gly Thr Tyr Arg Gly Pro Tyr Ile Tyr Arg Pro Thr Asp Ala
            20                  25                  30

Pro
```

( 2 ) INFORMATION FOR SEQ ID NO:6:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Asp Ala Pro Leu Pro Tyr Thr Gly Arg Tyr Asp Leu Asn Phe Asp Arg
 1               5                  10                  15

Trp Val Thr Val Asn Gly Tyr Lys Val Leu Tyr Arg Ser Leu Pro
            20                  25                  30
```

( 2 ) INFORMATION FOR SEQ ID NO:7:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Leu Tyr Arg Ser Leu Pro Phe Arg Glu Arg Leu Ala Arg Ala Arg Pro
1               5                   10                  15

Pro Trp Cys Val Leu Ser Gln Glu Glu Lys Asp Asp Met Lys Gln Gln
                20                  25                  30

( 2 ) INFORMATION FOR SEQ ID NO:8:

( i ) SEQUENCE CHARACTERISTICS:
    ( A ) LENGTH: 39 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

Lys Gln Gln Val His Asp Tyr Ile Tyr Leu Gly Thr Gly Met Ile His
1               5                   10                  15

Trp Lys Val Phe Tyr Asn Ser Arg Glu Glu Ala Lys Arg His Ile Ile
                20                  25                  30

Glu His Ile Lys Ala Leu Pro
            35

( 2 ) INFORMATION FOR SEQ ID NO:9:

( i ) SEQUENCE CHARACTERISTICS:
    ( A ) LENGTH: 44 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

Pro Asn Ser Asn Glu Gly Leu Ser Gln Gln Ser Thr Asp Pro Ser Pro
1               5                   10                  15

His Asn Phe Ile Leu Ser Asn Glu Asn Ser Tyr Pro Cys Tyr Ser Leu
                20                  25                  30

Leu Gly Asp Val Gln Arg Glu Asp Ser Thr Lys Phe
            35                  40

( 2 ) INFORMATION FOR SEQ ID NO:10:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:10:

Gly Lys Arg Lys Arg Gln Arg Arg Arg Lys Lys Lys Ala Phe Lys
1               5                   10                  15

Arg Met Met Thr Glu Leu Glu Asp Arg Phe Arg Lys Leu Phe
                20                  25                  30

(2) INFORMATION FOR SEQ ID NO:11:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Glu Leu Glu Asp Arg Phe Arg Lys Leu Phe Gly Thr Thr Ser Thr Thr
1               5                   10                  15

Gly Asp Ser Thr Val Asp Ser Glu Asp Glu Pro Pro Lys Lys Glu Lys
                20                  25                  30

Arg Val Asp
         35

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Gly Thr Thr Ser Thr Thr Gly Asp Ser Thr Val Asp Ser Glu Asp Glu
1               5                   10                  15

Pro Pro Lys Lys Glu Lys Arg Val Asp Trp Asp Glu Tyr Trp Asn Pro
                20                  25                  30

Glu Glu Ile
         35

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Glu Lys Arg Val Asp Trp Asp Glu Tyr Trp Asn Pro Glu Glu Ile Glu
1               5                   10                  15

Arg Met Leu Met
         20

(2) INFORMATION FOR SEQ ID NO:14:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Gly Gly Lys Trp Ser Lys Ser Ser Val Val Gly Trp Pro Thr Val
1               5                   10                  15

Arg Glu Arg Met Arg Arg Ala Glu Pro Ala Ala Asp Gly Val Gly Ala 20                    25                    30

Ala  Ser  Arg  Asp  Leu  Glu
              35

( 2 ) INFORMATION FOR SEQ ID NO:15:

( i ) SEQUENCE CHARACTERISTICS:
          ( A ) LENGTH: 35 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:15:

Gly  Ala  Ala  Ser  Arg  Asp  Leu  Glu  Lys  His  Gly  Ala  Ile  Thr  Ser  Ser
    1                   5                        10                       15

Asn  Thr  Ala  Ala  Thr  Asn  Ala  Ala  Cys  Ala  Trp  Leu  Glu  Ala  Gln  Glu
                   20                        25                       30

Glu  Glu  Glu
              35

( 2 ) INFORMATION FOR SEQ ID NO:16:

( i ) SEQUENCE CHARACTERISTICS:
          ( A ) LENGTH: 38 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:16:

Glu  Glu  Glu  Glu  Val  Gly  Phe  Pro  Val  Thr  Pro  Gln  Val  Pro  Leu  Arg
    1                   5                        10                       15

Pro  Met  Thr  Tyr  Lys  Ala  Ala  Val  Asp  Leu  Ser  His  Phe  Leu  Lys  Glu
                   20                        25                       30

Lys  Gly  Gly  Leu  Glu  Gly
                   35

( 2 ) INFORMATION FOR SEQ ID NO:17:

( i ) SEQUENCE CHARACTERISTICS:
          ( A ) LENGTH: 40 amino acids
          ( B ) TYPE: amino acid
          ( C ) STRANDEDNESS: single
          ( D ) TOPOLOGY: linear ( i i ) MOLECULE TYPE: peptide ( x i ) SEQUENCE DESCRIPTION: SEQ ID NO:17:

Glu  Lys  Gly  Gly  Leu  Glu  Gly  Leu  Ile  His  Ser  Gln  Arg  Arg  Gln  Asp
    1                   5                        10                       15

Ile  Leu  Asp  Leu  Trp  Ile  Tyr  His  Thr  Gln  Gly  Tyr  Phe  Pro  Asp  Trp
                   20                        25                       30

Gln  Asn  Tyr  Thr  Pro  Gly  Pro  Gly
                   35                  40

( 2 ) INFORMATION FOR SEQ ID NO:18:

( i ) SEQUENCE CHARACTERISTICS:
          ( A ) LENGTH: 38 amino acids
          ( B ) TYPE: amino acid
          ( C ) STRANDEDNESS: single
          ( D ) TOPOLOGY: linear -continued ( i i ) MOLECULE TYPE: peptide ( x i ) SEQUENCE DESCRIPTION: SEQ ID NO:18:

Asp Trp Gln Asn Tyr Thr Pro Gly Pro Gly Val Arg Tyr Pro Leu Thr
1               5                   10                  15

Phe Gly Trp Cys Tyr Lys Leu Val Pro Val Glu Pro Asp Lys Val Glu
                20                  25                  30

Glu Ala Asn Lys Gly Glu
            35

(2) INFORMATION FOR SEQ ID NO:19:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:19:

Asn Lys Gly Glu Asn Thr Ser Leu Leu His Pro Val Ser Leu His Gly
1               5                   10                  15

Met Asp Asp Pro Glu Arg Glu Val Leu Glu Trp Arg Phe Asp
                20                  25                  30

(2) INFORMATION FOR SEQ ID NO:20:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:20:

Glu Gln Arg Phe Asp Ser Arg Leu Ala Phe His His Val Ala Arg Glu
1               5                   10                  15

Leu His Pro Glu Tyr Phe Lys Asn Cys
                20                  25

RETROVIRAL SUPERANTIGENS, SUPERANTIGEN PEPTIDES, AND METHODS OF USE

This invention was made with government support under National Institutes of Health grant number AI25904. The government has certain rights in this invention.

BACKGROUND OF THE INVENTION

Normally, when a person's immune system encounters a protein made by a virus or other microbe, fewer than one in 10,000 of the white blood cells known as T lymphocytes react. Although their number is small, these T lymphocytes orchestrate an attack that specifically targets the alien protein, or antigen, without harming healthy tissue. In contrast, proteins called superantigens highly activate the immune system and can cause an unproductive, even destructive, immune response.

Superantigens are the most powerful T cell mitogens known (Johnson, H. M., H. I. Magazine [1988] *Int. Arch Allergy Appl. Immunol.* 87:87–90). As explained below, these unique antigens stimulate T cells by first binding to class II major histocompatibility (MHC) molecules (Carlsson, R., H. Fischer, H. O. Sjogren [1988] *J. Immunol.* 140:2484–2488; Fleischer, B., H. Schrezenmeier [1988] *J. Exp. Med.* 167:1697–1707; Mollick, J. A., R. G. Cook, R. R. Rich [1989] *Science* 244:817–820) and then as a binary complex bind in a $V_\beta$ specific manner to the T cell antigen receptor (TCR) (Janeway, C. A., J. Yagi, P. J. Conrad, M. E. Katz, B. Jones, S. Vroegop, S. Buxser [1989] *Immunol. Rev.* 107:61–88; White, J., A. Herman, A. M. Pullen, R. Kubo, J. W. Kappler, P. Marrack [1989] *Cell* 56:27–35).

Superantigens can arouse as many as one in five T cells, most of which are useless for fighting a current infection. What is worse, certain of the activated cells may unleash an autoimmune attack which targets tissues of the host organism. At times, superantigens may even have the opposite effect: they somehow trigger the death of the cells they excite.

Scientists have gleaned much of what they understand about superantigens from studying the earliest known examples: a group of structurally related proteins called staphylococcal enterotoxins (SEs). Staphylococcal enterotoxins account for as much as 45 percent of all cases of food poisoning. It is well established that when strains of the bacterium *Staphylococcus aureus* colonize food, they secrete one or more enterotoxins, which are now named alphabetically as A, B, C, D, and E. Within hours after people ingest badly contaminated, toxin-laden food, they begin to feel weak, feverish, and nauseated. Interestingly, intestinal tissue of affected patients looks virtually normal under the microscope. The only obvious abnormality is the presence of white cells in the tissue. It has now also been found that introduction of an enterotoxin to blood triggers the proliferation of lymphocytes. Just a few hundred molecules of toxin triggers a degree of replication that surpasses what could be achieved by a billion copies of a conventional antigen—for example, a protein on the influenza virus.

Further research has documented that a small amount of an enterotoxin can yield extraordinarily high production of chemical signals known as cytokines, which are produced by the subset of T lymphocytes called helper cells. These cells direct much of the immune response. The helper cells do not attack microbes themselves; instead they rely on the cytokines to activate both cytotoxic T lymphocytes, which kill infected cells, and B lymphocytes, which secrete antibodies against antigens.

By the mid-1980s it was recognized that when a tiny amount of enterotoxin A was mixed with T lymphocytes, the collection of cells produced a huge quantity of the cytokine known as interleukin-2 (IL-2). It has also been determined that infusion of high doses of IL-2 into the circulation of cancer patients (as part of an experimental therapy) causes the very symptoms associated with food poisoning. These data indicate that enterotoxins make people ill by stimulating production of high levels of interleukin-2.

Before helper T cells can recognize conventional protein antigens, the proteins must first undergo processing by macrophages or other antigen-presenting cells. These cells engulf antigens and process them into peptides. The presenters then display the peptide antigens at the cell surface in combination with major histocompatibility complex (MHC) class II molecules. A peptide fits in a cleft on an MHC molecule. Once an antigen is displayed, the few helper cells in the body that bear receptors for the particular peptide link up with it. Each T cell is specific for one kind of peptide antigen.

Like conventional toxins, enterotoxin superantigens can arouse helper cells only if antigen-presenting cells display the proteins to the T cells. Moreover, it is MHC class II molecules that do the presenting. Yet, unlike typical antigens, the enterotoxins bind MHC molecules directly; they do not require uptake and processing. Also, enterotoxins do not bind to the inner surface of the peptide-recognizing pocket of the MHC molecule, attaching instead to its outer surface. Then the MHC-superantigen unit contacts the T cell receptor at a site distinct from the surface that envelops conventional antigens. To be more precise, T cell receptors consist of two protein chains, alpha and beta. Both chains include structurally invariant and variable regions that participate in the binding of conventional peptide antigens. The enterotoxins are thought to link up with the beta-chain variable—or V-beta ($V_\beta$)—region, at a part not involved in the binding of typical antigens.

Each enterotoxin interacts with particular $V_\beta$ types. For instance, one enterotoxin may be recognized by the variable types numbered 5 and 12, whereas another might be recognized by types 12, 15, and 18. For example, SEB has been shown to be specific for T cells bearing $V_\beta$ elements such as 7 and 8.1–8.3 in mice (Herman, A., J. W. Kappler, P. Marrack, A. M. Pullen [1991] *Ann. Rev. Immunol.* 9:745–772). Investigators estimate that every human has fewer than 30 $V_\beta$ types, although the fraction of helper T cells carrying any given type can differ from person to person. A conventional antigen can activate only the relatively few helper cells specific for that antigen. A given enterotoxin, however, can activate many times that number of helpers (having a huge variety of peptide-antigen specificities) as long as the T cells bear selected $V_\beta$ types.

Although superantigens are suspected of, at times, causing over-activation of the immune system, some evidence suggests that superantigens may also depress the immune system. T cell clones aroused by superantigens often disappear (depletion) or become inactive (anergy) after being stimulated. Staphylococcal enterotoxins, the prototype superantigens, activate T cells bearing specific T cell antigen receptor β-chain variable region elements. Their $V_\beta$ specificity has profound implications with regard to expansion, anergy, and deletion of various T cell populations in terms of immunologic disease. It has been demonstrated that although an initial mitogenic effect is observed after in vivo administration of staphylococcal enterotoxin B (SEB), the lasting result appears to be both clonal anergy and deletion of $V_\beta$ specific peripheral T cells (Kawake, Y., A. Ochi [1991] *Nature* 349:245–248; Kawake, Y., A. Ochi [1990] *J. Exp. Med.* 172:1065–1070; Rellahan, B. L., L. A. Jones, A. M. Kruisbeek, A. M. Fry, L. A. Matis [1990] *J. Exp. Med.* 172:1092–1100).

Thus far, we have primarily focused on the interaction between superantigens and helper T cell activity; however, the possible deranging effects of superantigens on B cells should not be ignored. Staphylococcal enterotoxins sometimes enhance antibody production by B cells and sometimes inhibit it, depending on the initial state of immune arousal. Enhancement and suppression may each be destructive. Inhibition of antibody production can depress immune functioning. Overzealous production can lead to immune complex disorders, in which antibodies attract various components of the immune system to healthy tissue, clogging them and impeding normal function.

Interaction of the staphylococcal enterotoxins with class II molecules induces production of the cytokines tumor necrosis factor alpha (TNFα) and interleukin-1 (IL-1) by monocytes (Fischer, H., M. Dohlsten, U. Andersson, G. Hedlund, P. Ericsson, J. Hansson, H. O. Sjögren [1990] *J. Immunol.* 144:4663; Gjörloff, A., H. Fischer, G. Hedlund, J. Hansson, J. S. Kenney, A. C. Allison, H. O. Sjögren, M. Dohlsten [1991] *Cell Immunol.* 137:61). Both SEA and the related toxic shock syndrome toxin one (TSST-1) are potent inducers of TNFα and IL-1. Binding of these superantigens to MHC transduces a signal through the monocyte membrane which leads to tyrosine kinase activation and phosphorylation of multiple cytoplasmic proteins and monokine gene induction (Scholl, P. R., N. Trede, T. A. Chatila, R. S. Geha [1992] *J. Immunol.* 148:2237). Subsequently, monokines can have effects on T cells; for example, TNFα can further enhance human T cell proliferation (Yokota, S., T. D. Geppert, P. E. Lipsky [1988] *J. Immunol.* 140:531). IL-1 is an additional stimulator by increasing IL-2 secretion and IL-2 receptor expression. Both IL-1 and TNFα secretion may require the presence of T cells, particularly CD4$^+$ 45RO$^+$ memory T cells (Fischer et al., supra; Gjörloff et al., supra). A variety of peptide sequences of the superantigen SEA that participate in binding to the class II MHC molecules have previously been studied (Pontzer, C. H., J. K. Russell, H. M. Johnson [1989] *I Immunol.* 143:280; Pontzer, C., J. K. Russell, M. A. Jarpe, H. M. Johnson [1990] *Int. Arch. Allergy Appl. Immunol.* 93:107; Griggs, N. D., C. H. Pontzer, M. A. Jarpe, H. M. Johnson [1992] *J. Immunol.* 148:2516; Grossman, D., R. G. Cook, J. T. Sparrow, J. A. Mollick, R. R. Rich [1990] *I Exp. Med.* 172:1831; Grossman, D., M. Van, J. A. Mollick, S. K. Highlander, R. R. Rich [1991] *J. Immunol.* 147:3274).

Superantigens have been hypothesized to be associated with a number of pathological conditions. For example, superantigen alteration of the T cell repertoire has import for immunodeficiency and autoimmunity. T cells beating certain $V_\beta$ types have been implicated in various autoimmune conditions, including arthritis, lupus, and multiple sclerosis. It is conceivable, but not yet established, that over-activation of T cells by superantigens could play a role in certain autoimmune disorders.

Involvement of a predominant $V_\beta$ specific T cell population has been suggested for certain animal models of autoimmune disease. For example, experimental allergic encephalomyelitis (EAE) is an animal model for multiple sclerosis. Multiple sclerosis (MS) is a chronic, often disabling disease that attacks the central nervous system, damaging the protective coating that surrounds nerve fibers. EAE is mediated by $V_\beta 8.2^+$, CD4$^+$ T cells in PL/J mice after injection with myelin basic protein (MBP). This limited heterogeneity of TCR usage has implicated the involvement of $V_\beta 8.2^+$, CD4$^+$ T cells in EAE in PL/J mice immunized with rat myelin basic protein (Acha-Orbea, H., D. J. Mitchell, L. Timmerman, D. C. Wraith, G. S. Tausch, M. K. Waldon, S. S. Zamvil, H. O. McDevitt, L. Steinman [1988] *Cell* 54:263–273).

Recently, several novel immunological approaches have been explored relevant to autoimmune diseases such as EAE in mice and rats and lupus nephritis in MRL/lpr mice. Many have been directed toward blocking the function of the effector CD4$^+$ T cell which has been shown to exhibit $V_\beta$ isotype restriction in EAE. These approaches have included the use of anti-TCR antibodies (Acha-Orbea et al., supra), synthetic TCR peptides (Offner, H., G. A. Hashim, .A. A. Vandenbark [1991] *Science* 251:430–432) and superantigen treatment (Kim, C., K. A. Siminovitch, A. Ochi [1991] *J. Exp. Med.* 174:1431–1437).

Superantigens are also associated with retroviruses such as mouse mammary tumor virus (MMTV), and possibly human immunodeficiency virus (HIV), the virus responsible for AIDS. It has recently been reported that two exogenous strains of MMTV encode retroviral superantigens in the open reading frames (ORFs) of the 3' Long Terminal Repeat (LTR) of the viral genome (Pullen, A. M., Y. Choi, E. Kushnir, J. Kappler, P. Marrack [1992] *J. Exp. Med.* 175:41–47; Choi, Y., P. Marrack, J. Kappler [1992] *J. Exp. Med.* 175:847–851). There is preliminary evidence that the HIV genome may also encode a superantigen. It has been suggested that an HIV superantigen may target a subpopulation of CD4$^+$ T cells for HIV viral replication (Laurence, J., A. S. Hodtsev, D. N. Posnett [1992] *Nature* 358:255–259). HIV infection also results in the programmed cell death of CD4$^+$ T cells (apoptosis), both in vitro and in vivo, possibly as a result of an HIV protein with superantigen properties (Gougeon, M-L., L. Montagnier [1993] *Science* 260:1269–1270). Feline immunodeficiency virus (FIV) is a lentivirus which has been described extensively in the literature. See, for example, Kiyomasu, Takahiro, et al. (1991) "Identification of Feline Immunodeficiency Virus rev Gene Activity" *Journal of Virology* 65(8):4539–4542, and references cited therein. There has also been speculation that the human spumaretrovirus (HSRV) expresses a superantigen ("Molecular Biology of the Human Spumavirus," in *Human Retroviruses*, B. R. Cullen, ed., Oxford University Press, Oxford and New York, 1993, pp. 205–206).

Like many viruses, including MMTV and FIV, the HIV genome has a 3' Long Terminal Repeat. Initial studies indicated that a protein encoded by an ORF in the 3' LTR had negative effects on HIV replication in vitro, and hence was designated Negative Factor (NeF). NeF is a 25–29 kD protein that is mainly located the cytoplasm of HIV-infected cells, but is also associated with the plasma membrane (Allan, J. S., J. E. Coligan, T-H. Lee, M. F. McLane, P. J. Kanki, J. E. Groopman, M. Essex [1985] *Science* 230:810–813). The role of NeF in retrovital pathogenesis has been studied (Laurent, A. G., A. G. Hovanessian, Y. Riviere, b. Krust, A. Regnault, L. Montagnier, A. Findeli, M. P. Kieny, B. Guy [1990] *J. Gen. Virol.* 71:2273–2281). There are no reports that suggest NeF as a superantigen.

BRIEF SUMMARY OF THE INVENTION

The subject invention concerns the discovery of specific superantigen proteins and peptides and the use of these proteins and peptides as diagnostic reagents and in methods for modulating immune responses. More specifically, the subject invention concerns the discovery of superantigen proteins encoded in open reading frames (ORF) of the 3' Long Terminal Repeat (LTR) region of retroviruses. Specifically exemplified herein are superantigen proteins from the mouse mammary tumor virus (MMTV), feline immunodeficiency virus (FIV) and human immunodeficiency virus-1 (HIV-1).

A further aspect of the invention is the discovery of specific superantigen peptide fragments of the retroviral superantigen proteins. The superantigen nature of these peptides can be manifested in their ability to bind to known superantigen receptor sites, their reactivity with antibodies raised to superantigens, or their own ability to elicit an immune response characteristic of superantigens. For example, the MMTV and HIV-derived superantigen peptides of the subject invention are able to block the binding of $^{125}$I-labelled superantigen staphylococcal enterotoxin A (SEA) to class II MHC-bearing cells by binding to a region on the MHC molecule where SEA normally binds. An FIV superantigen peptide has also been discovered which reacts with antibodies known to be associated with FIV infection.

In one embodiment of the subject invention, we have identified a superantigen peptide, designated herein as MMTV ORF (76–119) [SEQ ID NO. 1], derived from the MMTV 3' LTR ORF superantigen. We have discovered that this peptide binds to the same region on the β-chain of class II MHC molecules as does the SEA superantigen. As described herein, the MMTV ORF superantigen peptide is useful for inducing an immune response in vitro or in an animal in need of such a response.

Another aspect of the subject invention is the discovery of an FIV superantigen which has not previously been isolated or characterized. The FIV superantigen is encoded by a sequence within the 3' LTR ORF of the genome of the FIV virus. We have also identified two peptides, FIV ORF4 (1–30) [SEQ ID NO. 10] and FIV ORF4 (21–55) [SEQ ID NO. 11], derived from the 3' LTR ORF4 of FIV, that are recognized by the antisera of both FIV-vaccinated and FIV-infected cats. In addition, the FIV ORF4(1–30) [SEQ ID NO. 10] peptide can be used as an immunoaffinity reagent to purify viral neutralizing antibodies from FIV-infected cat sera. Thus, the FIV ORF4 superantigen peptides of the subject invention can be used to detect FIV-induced antibodies and as an immunoaffinity reagent to purify anti-FIV antibodies. These peptides can also be used to raise an immune response.

The HIV-1 superantigen of the subject invention corresponds to the HIV-1 Negative Factor (NeF) protein which has never before been recognized to have superantigen properties. We have discovered that the HIV-1 NeF protein induces a rapid proliferation of cells, followed by a non-proliferative phase that results in substantial cell death. Also, we have identified a peptide fragment of the HIV-1 NeF protein, designated here as HIV-1 NeF(123–160) [SEQ ID NO. 18], which binds to human class II MHC. Thus, in one embodiment of the subject invention, the NeF superantigen protein or peptide can be used to raise an immune response in an animal in need of such a response.

The ability of peptide superantigen agonists to alter the T cell repertoire has implications for the treatment of a variety of immunologic disease states such as immunodeficiency and autoimmunity. While immunotherapy using the whole superantigen molecule could produce non-specific effects and potentially undesirable side effects, peptide agonists and antagonists of superantigen function can target components of the immune system, alter function, and achieve therapeutic ends. The peptides can also be used in diagnostic procedures to detect the presence of superantigens or antibodies that are immunoreactive with superantigens.

BRIEF DESCRIPTION OF THE SEQUENCES

Figure 1:
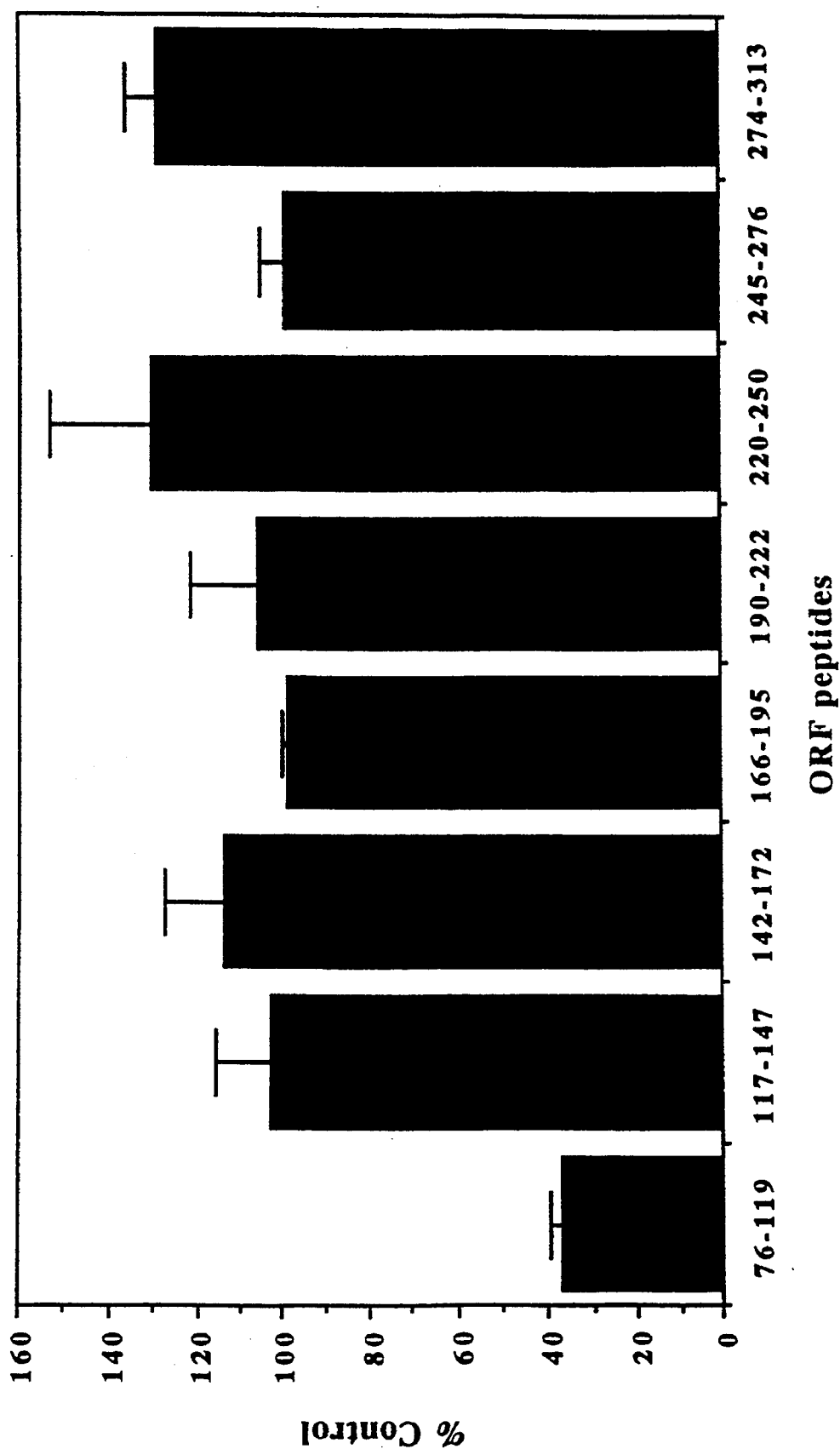
FIG. 1. Competitive binding of MMTV ORF peptides to mouse A20 cells. Competitor peptides were used at a final concentration of 200 μM. $^{125}$I-SEA was added at a final concentration of 2.5 nM. Binding of $^{125}$I-SEA in the absence of competitors was 6,384±400 CPM. The data presented represent the mean of three individual experiments each performed in duplicate. Each bar represents the mean percent reduction of SEA control binding in the presence of ORF peptides± standard deviation.

SEQ ID NO. 1 is the amino acid sequence of an MMTV ORF peptide designated MMTV ORF(76–119).

SEQ ID NO. 2 is the amino acid sequence of an MMTV ORF peptide designated MMTV ORF(117–147).

SEQ ID NO. 3 is the amino acid sequence of an MMTV ORF peptide designated MMTV ORF(142–172).

SEQ ID NO. 4 is the amino acid sequence of an MMTV ORF peptide designated MMTV ORF(166–195).

SEQ ID NO. 5 is the amino acid sequence of an MMTV ORF peptide designated MMTV ORF(190–222).

SEQ ID NO. 6 is the amino acid sequence of an MMTV ORF peptide designated MMTV ORF(220–250).

SEQ ID NO. 7 is the amino acid sequence of an MMTV ORF peptide designated MMTV ORF(245–276).

SEQ ID NO. 8 is the amino acid sequence of an MMTV ORF peptide designated MMTV ORF(274–313).

SEQ ID NO. 9 is a scrambled amino acid sequence of MMTV ORF(76–119) [SEQ ID NO. 1] and is designated MMTV ORF(76–119) scrambled.

SEQ ID NO. 10 is the amino acid sequence of an FIV ORF4 peptide designated FIV ORF4 (1–30).

SEQ ID NO. 11 is the amino acid sequence of an FIV ORF4 peptide designated FIV ORF4 (21–55).

SEQ ID NO. 12 is the amino acid sequence of an FIV ORF4 peptide designated FIV ORF4 (31–65).

SEQ ID NO. 13 is the amino acid sequence of an FIV ORF4 peptide designated FIV ORF4 (51–71).

SEQ ID NO. 14 is the amino acid sequence of an HIV-1 NeF peptide designated HIV-1 NeF (1–38).

SEQ ID NO. 15 is the amino acid sequence of an HIV-1 NeF peptide designated HIV-1 NeF (31–65).

SEQ ID NO. 16 is the amino acid sequence of an HIV-1 NeF peptide designated HIV-1 NeF (62–99).

SEQ ID NO. 17 is the amino acid sequence of an HIV-1 NeF peptide designated HIV-1 NeF (93–132).

SEQ ID NO. 18 is the amino acid sequence of an HIV-1 NeF peptide designated HIV-1 NeF (123–160).

SEQ ID NO. 19 is the amino acid sequence of an HIV-1 NeF peptide designated HIV-1 NeF (156–186).

SEQ ID NO. 20 is the amino acid sequence of an HIV-1 NeF peptide designated HIV-1 NeF (182–206).

DETAILED DESCRIPTION OF THE INVENTION

The subject invention pertains to new compositions and methods utilizing viral superantigens and superantigen peptides. Specifically, these superantigens and superantigen peptides have been discovered within the 3' long terminal repeat (LTR) of several retroviruses. In specific embodiments of the subject invention, we have discovered superantigens and superantigen peptides from the mouse mammary tumor virus (MMTV), feline immunodeficiency virus (FIV), and human immunodeficiency virus (HIV).

This invention is the first report of specific superantigen sequences from either FIV or HIV, and it is the first report of any superantigen peptide agonists from retroviruses. The peptides described herein are particularly advantageous because they facilitate specific manipulation of the immune system. Because of the involvement of autoimmune processes in various disease states such as diabetes, multiple sclerosis, lupus, and rheumatoid arthritis, the peptides of the subject invention provide advantageous therapeutic agents. These peptides can also be used in diagnosing and treating various autoimmune and retroviral-induced disorders. The peptides can also be used to produce antagonists to proteins having superantigen activity, and to produce polyclonal and monoclonal antibodies that specifically bind to the superantigen from which the peptide was derived.

The term "superantigen" is being used herein as denoting a molecule that would typically have the following properties: (1) A molecule that binds directly to class II MHC in a region outside of the antigen-binding groove on the MHC molecule, (2) which then binds as a binary complex to the T cell antigen receptor in a Vβ-specific manner, and (3) thereby stimulates the proliferation of the T cells bearing those specific Vβ types. Typically, the superantigen will effectively compete with Staphylococcal enterotoxins for binding to a class II MHC molecule.

The MMTV superantigen is encoded in an open reading frame (ORF) of the 3' Long Terminal Repeat (LTR) of the MMTV viral genome. The MMTV superantigen is believed to be a 45 kD type II integral membrane protein with a glycosylated extracellular C-terminus and an intracellular N-terminus (Choi, Y., P. Marrack, J. W. Kappler [1992] *J. Exp. Med.* 175:847–851). As described in more detail below, overlapping peptides corresponding to the amino acid sequence of the predicted extracellular domain of the MMTV ORF superantigen were synthesized (designated here as MMTV ORF): MMTV ORF(76–119) [SEQ ID NO. 1], MMTV ORF(117–147) [SEQ ID NO. 2], MMTV ORF(142–172) [SEQ ID NO. 3], MMTV ORF(166–195) [SEQ ID NO. 4], MMTV ORF(190–222) [SEQ ID NO. 5], MMTV ORF(220–250) [SEQ ID NO. 6], MMTV ORF(245–276) [SEQ ID NO. 7], and MMTV ORF(274–313) [SEQ ID NO. 8]. These peptides are shown in Table 1.

TABLE 1

Amino acid sequences of MMTV ORF peptides

| ORF peptide | Sequence |
| --- | --- |
| MMTV ORF(76–119) | SEQ ID NO. 1 f DSFNNSSVQDYNLNDSENSTFLLGQGPQPTSSYKPHRLCPSEIE |
| MMTV ORF(117–147) | SEQ ID NO. 2 f EIEIRMLAKNYIFTNETNPIGRLLIMMLRNE |
| MMTV ORF(142–172) | SEQ ID NO. 3 f MMLRNESLSFSTIFTQIQRLEMGIENRKRRS |
| MMTV ORF(166–195) | SEQ ID NO. 4 f ENRKRRSTSVEEQVQGLRASGLEVKRGKRS |
| MMTV ORF(190–222) | SEQ ID NO. 5 f KRGKRSALVKIGDRWWQPGTYRGPYIYRPTDAP |
| MMTV ORF(220–250) | SEQ ID NO. 6 f DAPLPYTGRYDLNFDRWVTVNGYKVLYRSLP |
| MMTV ORF(245–276) | SEQ ID NO. 7 f LYRSLPFRERLARARPPWCVLSQEEKDDMKQQ |
| MMTV ORF(274–313) | SEQ ID NO. 8 f KQQVHDYIYLGTGMIHWKVFYNSREEAKRHIIEHIKALP |
| MMTV ORF(76–119) scrambled | SEQ ID NO. 9 f PNSNEGLSQQSTDPSPHNFILSNENSYPCYSLLGDVQREDSTKF |

The peptides shown in Table 1 were tested at a concentration of 200 μM for their ability to compete with $^{125}$I-SEA for binding to A20 cells, a cell line that expresses I-A$^d$ and I-E$^d$. MMTV ORF(76–119) [SEQ ID NO. 1] reduced the binding of $^{125}$I-SEA by approximately 63% (FIG. 1). None of the other MMTV ORF peptides were able to reduce $^{125}$I-SEA binding at the concentration tested. In a dose response study, the MMTV ORF(76–119) [SEQ ID NO. 1] peptide was able to reduce $^{125}$I-SEA binding to A20 cells by approximately 50% at concentrations as low as 20 μM. Additionally, a radioimmunoassay was performed to determine if the competition observed with MMTV ORF(76–119) [SEQ ID NO. 1] was due to the direct binding of the peptide to the A20 cells. $^{125}$I-MMTV ORF(76–119) [SEQ ID NO. 1] did bind to the A20 cells and was effectively inhibited by both unlabeled SEA and unlabeled MMTV ORF(76–119) [SEQ ID NO. 1]. Unlabeled SEA and MMTV ORF(76–119) [SEQ ID NO. 1] competed with $^{125}$I-MMTV ORF(76–119) [SEQ ID NO. 1] in a similar manner, although SEA was a more potent competitor. SEA reduced $^{125}$I-MMTV ORF(76–119) [SEQ ID NO. 1] binding by 50% at a concentration of 1.8 μM as compared to 25 μM for unlabeled MMTV ORF(76–119) [SEQ ID NO. 1]. An MMTV ORF(76–119) scrambled [SEQ ID NO. 9] peptide did not compete, indicating that MMTV ORF(76–119) [SEQ ID NO. 1] binding to A20 cells is sequence specific. Toxic shock syndrome toxin-1 (TSST-1) did not compete with $^{125}$I-MMTV ORF(76–119) [SEQ ID NO. 1], whereas the staphylococcal enterotoxin B (SEB) competed less effectively than SEA. This evidence indicates that MMTV ORF(76–119) [SEQ ID NO. 1] binds to murine class II molecules at a region where SEA also binds.

Binding experiments using class II-positive (A20 cells) and class II-negative (L cells) cell lines demonstrated that binding of MMTV ORF(76–119) [SEQ ID NO. 1] peptide to the class II-negative L cell line is insignificant in comparison to MMTV ORF(76–119) [SEQ ID NO. 1] binding to A20 cells. In addition, antibodies that specifically bind to class II antigens were able to significantly block binding of the MMTV ORF(76–119) [SEQ ID NO. 1] peptide A20 cells, whereas antibodies specific for class I MHC did not block binding of the peptide. When polyclonal I-A$^d$ and Ia.7 antibodies were used in combination, the binding of the MMTV ORF(76–119) [SEQ ID NO. 1] peptide to A20 cells was reduced by 73%. These antibodies can be obtained from the NIH.

A competitive radioimmunoassay using a peptide corresponding to amino acid residues 60–90 of the class II MHC β-chain was performed to directly determine whether MMTV ORF(76–119) [SEQ ID NO. 1] binds to the β1 helix of the I-A molecule, the same region that SEA binds to on the molecule. SEA and MMTV ORF(76–119) [SEQ ID NO. 1] competed with both $^{125}$I-SEA and $^{125}$I-MMTV ORF(76–119) [SEQ ID NO. 1] for binding to the I-Aβ$^b$(60–90) peptide in a manner similar to the competition observed on whole cells. Therefore, the data indicate that, despite the diverse origins of SEA and MMTV superantigens, SEA protein and MMTV ORF(76–119) [SEQ ID NO. 1] peptide bind to a similar region on the β-chain of murine class II MHC molecules, and, thus, the MMTV ORF peptide is a powerful tool for modulation of the immune response.

The subject invention further concerns the discovery of a superantigen and superantigen peptides from the feline immunodeficiency virus (FIV). The FIV ORF4 encodes a protein consisting of 71 amino acid residues. However, the protein product of this gene has never been shown to be expressed. Four overlapping peptides corresponding to the entire sequence of the FIV ORF4 which is found in the 3' Long Terminal Repeat region of FIV were synthesized (designated here as FIV ORF4): FIV ORF4(1–30) [SEQ ID NO. 10], FIV ORF4(21–55) [SEQ ID NO. 11], FIV ORF4(31–65) [SEQ ID NO. 12] and FIV ORF4(51–71) [SEQ ID NO. 13]. These peptides are shown in Table 2.

Each FIV ORF4 peptide of the subject invention was tested in an ELISA assay to determine whether antisera from cats vaccinated with FIV, and having high viral-neutralizing titers, would react with any of the ORF4 peptides. Serum from a virus-vaccinated cat showed high reactivity to FIV ORF4(1–30) [SEQ ID NO. 10], but significantly less reactivity to FIV ORF4(21–55) [SEQ ID NO. 11]. There was no reactivity to either of the C-terminal peptides. A similar pattern of reactivity was observed with sera from a cell-vaccinated cat, although the reactivity was weaker than with the virus-vaccinated cat sera. Pooled sera from control cats did not react with any of the ORF4 peptides.

Figure 4:
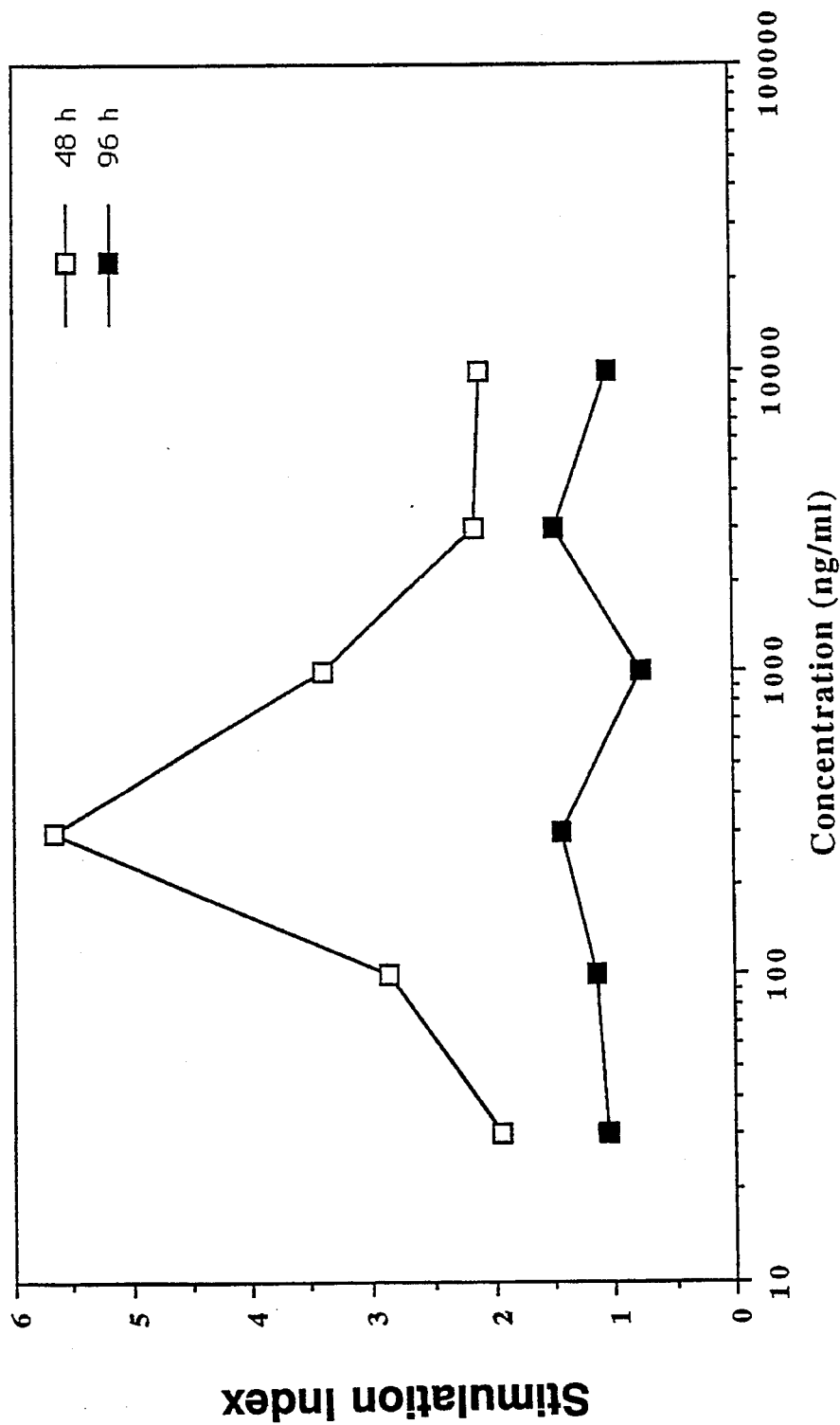
FIG. 4. Proliferative response of peripheral mononuclear cells to HIV-1 NeF protein. Cell proliferation was measured at 48 (□) and 96 (■) hours after the cell culture was initiated.

The reactivity of pooled antisera from cats infected with FIV (Petaluma strain), drawn at various intervals post-infection, was tested for reactivity to the FIV ORF4 peptides. All four of the ORF4 peptides reacted with the antisera. Reactivity to all four peptides peaked at 10 weeks post-infection, followed by a decline to a plateau level. However, a second peak of reactivity for all of the ORF4 peptides, except FIV ORF4(1–30) [SEQ ID NO. 10], was observed with antisera drawn at about 220 weeks post-infection (FIG. 4).

Figure 5:
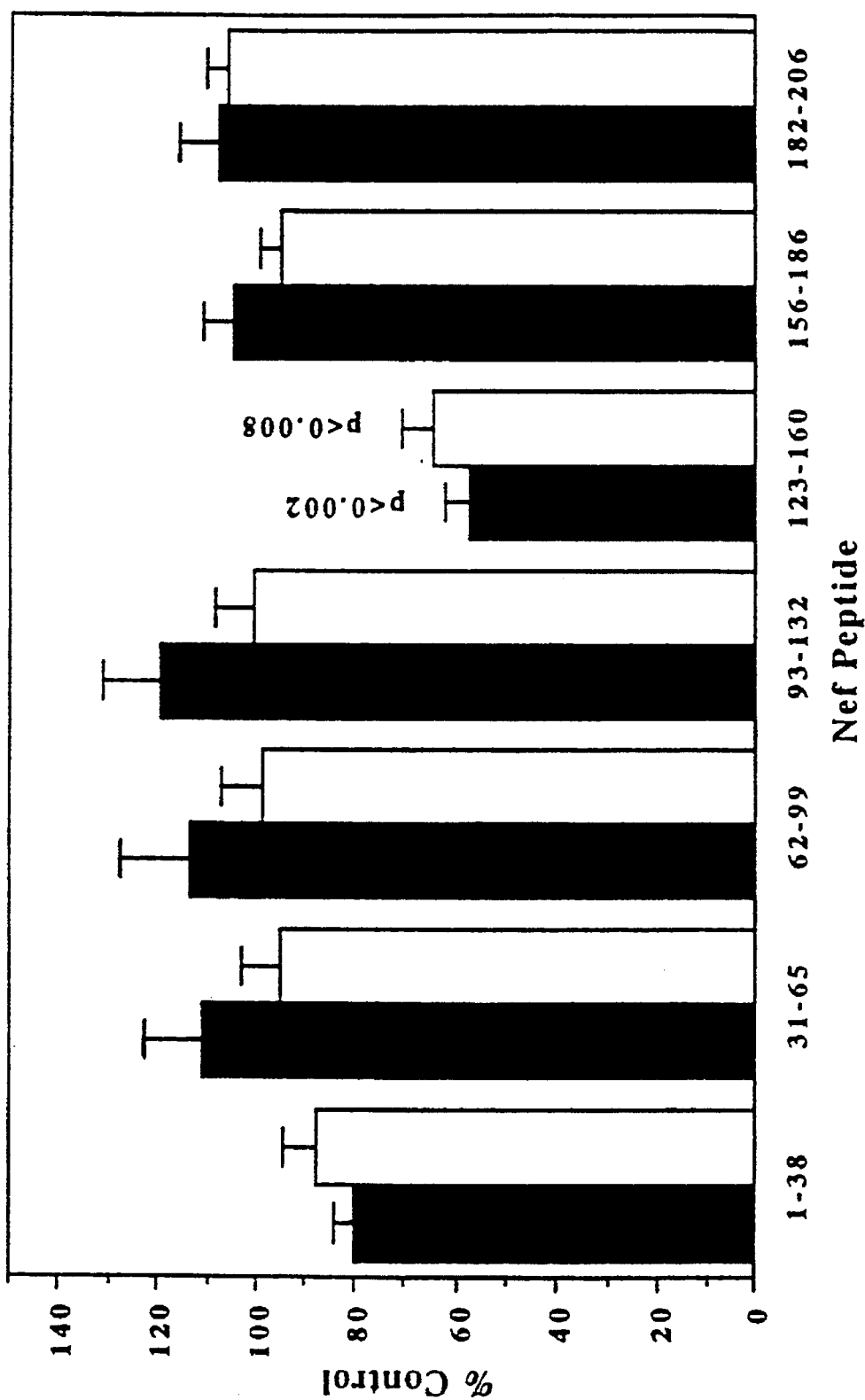
FIG. 5. Blockage of $^{125}$I-SEA binding to Raji and DR1-transfected L cells by HIV-1 Nef peptides. HIV-1 Nef peptides were used at a final concentration of 300 μM. $^{125}$I-SEA was used at a final concentration of 2 nM. $10^5$ Raji or DR1-transfected L cells were used per tube. Binding of $^{125}$I-SEA to Raji and DR1-transfected L cells in the absence of competitors was 31,469±2292 and 5,708±41 CPM, respectively. Data represent the mean percent of control of three individual experiments, each performed in duplicate. Bars represent binding to Raji (■) and DR1-transfected L cells (□) in the presence of Nef peptides±SD.

The subject invention further concerns the discovery of a superantigen and superantigen peptides from the human immunodeficiency virus (HIV-1). The HIV-1 NeF protein is one of the earliest proteins synthesized during viral replication. The HIV-1 NeF protein was tested at various concentrations in a proliferation assay to determine its effects on human peripheral mononuclear cells (PMNC's). NeF protein increased cell proliferation several fold over basal level when measured at 48 hours after initiation of the cell culture. However, 96 hours after culture initiation, there was no cell proliferation, and in fact, substantial cell death was observed (FIG. 5).

The same approach used for the MMTV and FIV peptides was used to synthesize overlapping peptides corresponding to the sequence of the HIV-1 NeF protein (designated here as HIV-1 NeF): HIV-1 NeF(1–38) [SEQ ID NO. 14], HIV-1 NeF(31–65) [SEQ ID NO. 15], HIV-1 NeF(62–99) [SEQ ID NO. 16], HIV-1 NeF(93–132) [SEQ ID NO. 17], HIV-1 NeF(123–160)[SEQ ID NO. 18], HIV-1 NeF(156–186) [SEQ ID NO. 19] and HIV-1 NeF(182–206) [SEQ ID NO. 20]. These peptides are shown in Table 3.

TABLE 2

FIV ORF4 peptide sequence

| Peptide | Sequence |
| --- | --- |
| FIV ORF4 (1–30) | SEQ ID NO. 10 f GKRKRQRRRRKKKAFKRMMTELEDRFRKLF |
| FIV ORF4 (21–55) | SEQ ID NO. 11 f ELEDRFRKLFGTTSTTGDSTVDSEDEPPKKEKRVD |
| FIV ORF4 (31–65) | SEQ ID NO. 12 f GTTSTTGDSTVDSEDEPPKKEKRVDWDEYWNPEEI |
| FIV ORF4 (51–71) | SEQ ID NO. 13 f EKRVDWDEYWNPEEIERMLM |

TABLE 3

Amino acid sequences of HIV-1 NeF peptides

| NeF PEPTIDE | SEQUENCE |
| --- | --- |
| HIV-1 NeF (1–38) | SEQ ID NO. 14 f MGGKWSKSSVVGWPTVRERMRRAEPAADGVGAASRDLE |
| HIV-1 NeF (31–65) | SEQ ID NO. 15 f GAASRDLEKHGAITSSNTAATNAACAWLEAQEEEE |
| HIV-1 NeF (62–99) | SEQ ID NO. 16 f EEEEVGFPVTPQVPLRPMTYKAAVDLSHFLKEKGGLEG |
| HIV-1 NeF (93–132) | SEQ ID NO. 17 f EKGGLEGLIHSQRRQDILDLWIYHTQGYFPDWQNYTPGPG |
| HIV-1 NeF (123–160) | SEQ ID NO. 18 f DWQNYTPGPGVRYPLTFGWCYKLVPVEPDKVEEANKGE |
| HIV-1 NeF (156–186) | SEQ ID NO. 19 f NKGENTSLLHPVSLHGMDDPEREVLEWRFD |
| HIV-1 NeF (182–206) | SEQ ID NO. 20 f EQRFDSRLAFHHVARELHPEYFKNC |

Figure 2:
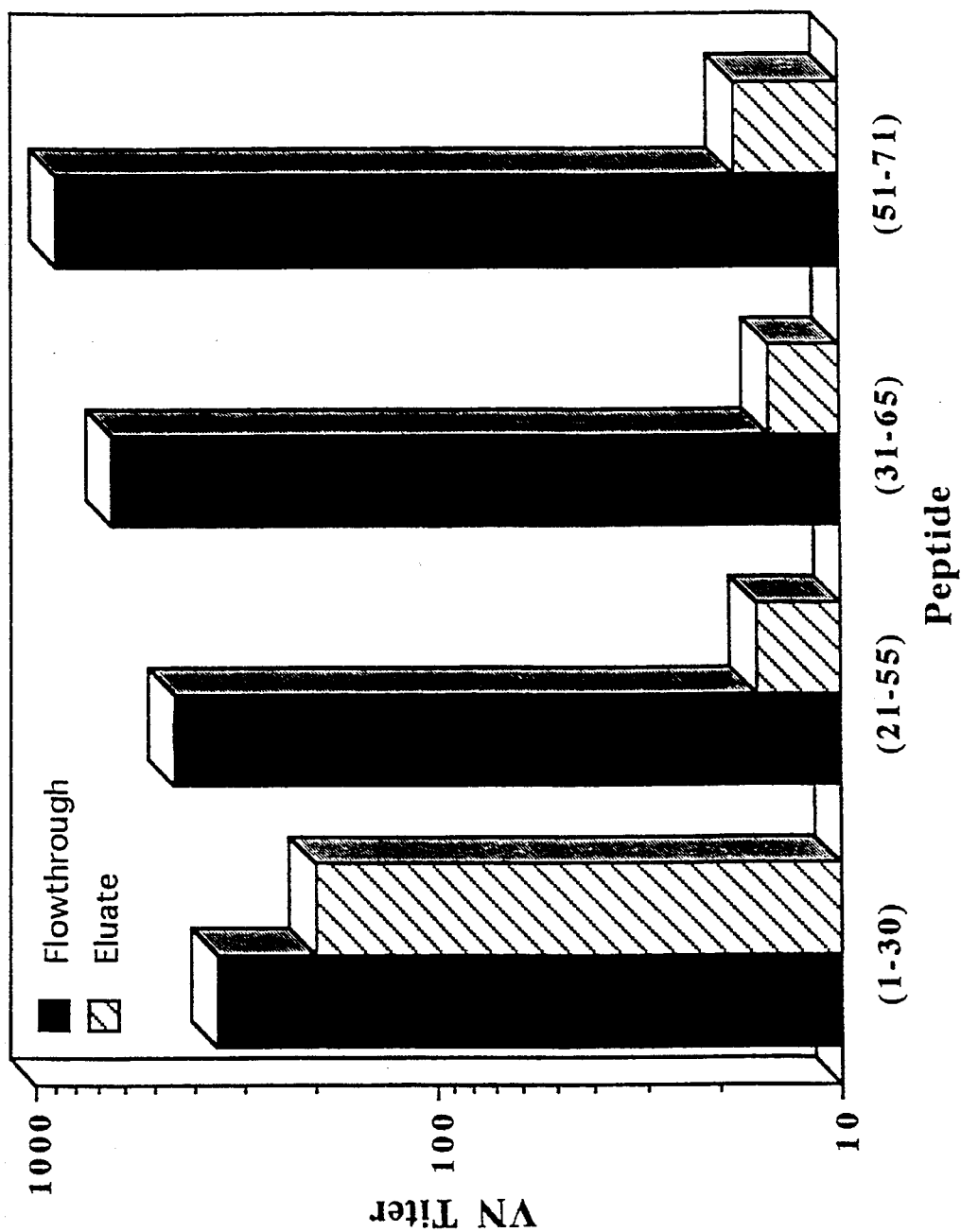
FIG. 2. FIV neutralization by anti-peptide reactive antibodies purified using FIV ORF4 peptide immunoaffinity columns. The viral neutralizing (VN) titer of antibodies isolated from pooled sera of FIV-vaccinated cats is shown for the flow-through and the eluate of each FW peptide immunoaffinity column.

The HIV-1 NeF(123–160) [SEQ ID NO. 18] peptide was found to block the binding of $^{125}$I-SEA to Raji cells, a human cell line that expresses class II MHC molecules on its surface (FIG. 2). At the highest concentration tested, 300 μM, HIV-1 NeF(123–160) [SEQ ID NO. 18] peptide reduced the binding of $^{125}$I-SEA to Raji cells by approximately 40%, and competed with SEA in a dose-dependent manner. HIV-1 NeF(1–38) [SEQ ID NO. 14] and HIV-1 NeF(31–65) [SEQ ID NO. 15] had slight inhibitory effects on $^{125}$I-SEA binding when the peptides were present at a concentration of 300 μM. Unlabeled SEA reduced $^{125}$I-SEA binding by 50% at a concentration of 2 μM, a reduction that is consistent with the reported Kd of SEA for HLA molecules.

The HIV-1 NeF(123–160) [SEQ ID NO. 18] peptide was also tested to determine whether there was direct binding to Raji cells. Unlabeled HIV-1 NeF(123–160) [SEQ ID NO. 18] reduced $^{125}$I-HIV-1 NeF(123–160) [SEQ ID NO. 18] binding by 50% at a concentration of 30 μM, and unlabeled SEE reduced $^{125}$I-HIV-1 NeF(123–160) [SEQ ID NO. 18] binding by 50% at a concentration of 2 μM. Unlabeled SEA did not inhibit $^{125}$I-HIV-1 NeF(123–160) [SEQ ID NO. 18] binding as well as SEE, but it was more effective than $SEC_1$ or SEB. This data demonstrates that HIV-1 NeF(123–160) [SEQ ID NO. 18] peptide competes for sites on MHC class II molecules that are more closely associated with sites where SEE binds to the class II molecule than sites where the other SEs bind.

Monoclonal antibodies specific to class I and class II antigens were used to determine which receptors the $^{125}$I-HIV-1 NeF(123–160) [SEQ ID NO. 18] peptide was binding on Raji cells. Clone L243, a monoclonal antibody specific for HLA-DR, reduced $^{125}$I-HIV-1 NeF(123–160) [SEQ ID NO. 18] binding by about 35%. Anti-HLA-DR monoclonal antibodies from clone L227 reduced peptide binding, but not as effectively as clone L243. Antibodies to class I antigens had no effect on $^{125}$I-HIV-1 NeF(123–160) [SEQ ID NO. 18] binding. These antibodies are available from Becton Dickinson, Mountain View, Calif. The data indicate that HIV-1 NeF(123–160) [SEQ ID NO. 18] peptide binds directly to class II MHC molecules, the known receptors for superantigens on antigen-presenting cells.

The discovery of a peptide agonist, especially of T cell function, is highly unexpected. As a condition of agonist activity, the peptide must bind to MHC and TcR, and thus compete for binding with a native superantigen molecule. Use of synthetic peptide agonists and antagonists rather than the whole superantigen molecule offers advantages such as a lack of side effects and targeting of immune system components. Also, specific amino acid residues can be easily and rapidly modified to allow for generation of more effective agonists or antagonists.

As those skilled in the art can readily appreciate, there can be a great number of natural variants of retroviral sequences, in addition to those variants that can be artificially created by the skilled artisan in the lab. The sequences of naturally-occurring variants can be readily obtained from the Los Alamos Database on Human Retroviruses. The proteins and peptides of the subject invention encompasses those specifically exemplified herein, as well as any natural variants thereof, as well as any variants which can be created artificially. Of particular interest are the conserved regions of retroviral superantigen sequences.

The peptides claimed according to the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or removed from, either end of the disclosed peptides. Preferably, any added amino acids would be the same as the corresponding amino acids of a native retroviral protein. Such a longer or shorter peptide would be within the scope of the subject invention as long as said peptide is shorter than the full length retroviral protein and said longer or shorter peptide retains substantially the same relevant biological activity as the peptides exemplified herein. For example, a longer or shorter variant of the HIV-1 NeF( 123–160) [SEQ ID NO. 18] peptide would fall within the scope of the subject invention if said variant had the ability to block the binding of SEA superantigen to class II MHC molecules. Also within the scope of the subject invention are peptides which have the same amino acid sequences of a peptide exemplified herein except for amino acid substitutions, additions, or deletions, as long as these variant peptides retain substantially the same relevant biological activity as the peptides specifically exemplified herein. For example, conservative amino acid substitutions within a peptide which do not affect the ability of the peptide to, for example, block the binding of SEA to class II MHC molecules would be within the scope of the subject invention. The peptides designated herein by the "viral peptide" designation, i.e., MMTV ORF(76–119), FIV ORF4(1–30), HIV-1 NeF(123–160), etc., should be understood to include variants and fragments, as discussed above, of the specifically exemplified sequences.

The subject invention further includes nucleotide sequences which encode the superantigen proteins and peptides disclosed herein. These nucleotide sequences could be readily constructed by those skilled in the art having the knowledge of the protein and peptide sequences which are presented herein. As would be appreciated by one skilled in the art, a variety of nucleotide sequences could be constructed to encode a particular peptide or protein due to the degeneracy of the genetic code. The choice of a particular nucleotide sequence could depend, for example, upon the codon usage of a particular expression system.

As described herein, the peptide sequences of the subject invention can also be the basis for producing peptide antagonists. These antagonists are also within the scope of the subject invention. Inhibition or antagonism of retroviral superantigen function without agonist activity can be accomplished through the use of anti-peptide antibodies or modification of residues within the peptide itself. An especially productive means for generation of peptide antagonists has been substitution of L-amino acids with D-amino acids. The efficacy of this approach has been well characterized in the generation of arginine vasopressin analogs with selectively enhanced antidiuretic antagonism by appropriate substitution of L- with D-amino acids (Manning, M., W. H. Sawyer [1985] In: *Vasopressin*, Schrier, R. W., ed., Raven Press, New York, pp. 131–144). Further, not only can antagonism be produced with D-amino acid substitutions, but this antagonism can be directed toward a specific function. This targeting is desirable for superantigen antagonism because of the numerous superantigen activities. The binding affinity/avidity and specific activity of our agonist and antagonist peptides can be further enhanced through chemical synthesis of multivalent forms of the agonist and/or antagonist peptides of superantigen activity. Production of potent antagonist peptides will be of value in specifically manipulating immune function and in protection from superantigen-induced disease.

A further aspect of the claimed invention is the use of the claimed peptides to produce antibodies. These antibodies can be produced using standard procedures well known to those skilled in the art. These antibodies may be used as diagnostic and therapeutic reagents. For example, antibodies that bind to the HIV-1 NeF protein may be used as an antagonist to inhibit the deleterious effects of the NeF protein. The subject invention also includes antibodies that bind to class II MHC molecules and effectively prevent the binding of a retroviral superantigen, or a peptide fragment thereof, to class II MHC molecules. These antibodies can also be produced using procedures that are commonly employed by those skilled in the art.

The peptides are also useful as vaccines to prevent retroviral infections in non-infected individuals, and as immunotherapeutic reagents to help control retroviral pathogenesis in individuals already infected by a retrovirus. For example, to the extent that the HIV-1 NeF superantigen is required for infection and progress of the disease state, then antagonists of NeF activity can be used to help control the progression of AIDS, as well as to prevent infection.

In addition to their use in treating various disease states, the peptides can also be used to detect the presence of antibodies that are reactive with retroviral superantigen proteins in serum or other bodily fluid samples. The peptides of the subject invention are also useful for stimulating peripheral mononuclear cells in vitro. This can be important, for example, in a variety of diagnostic procedures.

The teachings provided herein can be used by those skilled in the an to locate agonist and antagonist peptides from other retroviral superantigens.

MATERIALS AND METHODS

Reagents. Raji cells are EBV-transformed B cells that express DR3, Dw10, DQw1, and DQw2. L cells and mouse A20 cells were obtained from the American Type Culture Collection (ATCC) in Rockville, Md.

SEA was obtained from Toxin Technology (Sarasota, Fla.). Polymyxin B was obtained from Sigma Chemical Co. (St. Louis, Mo.). Purified recombinant NeF protein was obtained from Repligen Corporation (Cambridge, Mass.).

Synthetic peptides. Overlapping peptides corresponding to a region within the MMTV superantigen, amino acids 76–119, 117–147, 142–172, 166–195, 190–222, 220–250, 245–276, and 274–313 were synthesized. The amino acid sequence of the MMTV ORF was derived from Pullen, A. M., Y. Choi, E. Kushnir, J. Kappler, P. Marrack, [1992] *J. Exp. Med.* 175:41–47. In addition, a peptide with a scrambled sequence of amino acids 76–119 was synthesized. The MMTV ORF(76–119) [SEQ ID NO. 1] scrambled peptide sequence was generated using the sequence edit program of Devereax, J., P. Haeberli, O. Smithies [1984] *Nucleic Acids Res.* 12:387–395.

Overlapping peptides corresponding to the entire FIV ORF4 region, amino acids 1–30, 21–55, 31–65, and 51–71 were synthesized. The amino acid sequence of the FIV ORF4 peptides was obtained from Olmstead, R. A., V. M. Hirsch, R. H. Purcell, P. R. Johnson [1989] *Proc. Natl. Acad. Sci. USA* 86:8088–8092.

Overlapping peptides corresponding to the entire HIV-1 NeF protein, amino acids 1–38, 31–65, 62–99, 93–132, 123–160, 156–186, and 182–206 were synthesized. The amino acid sequence of the NeF peptides was based on the LAV strain of HIV-1 (this strain is also referred to as the HIVLAI strain in the Los Alamos Database) and was obtained from Wain-Hobson, S., P. Sonigo, O. Danos, S. Cole, M. Alizon [1985] *Cell* 40:9–17. Sequences of the NeF protein of other HW-1 strains can be obtained from the Los Alamos Database on Human Retroviruses.

All peptides were synthesized using a Biosearch 9500AT automated peptide synthesizer using N-(9-flurenyl) methoxycarbonyl chemistry (Chang, C. D., J. Meienhofer [1978] *Int. J. Peptide Protein Res.* 11:246). Peptides were cleaved from the resins using trifluoroacetic acid/ethanedithiol/thioanisole/anisole at a ratio of 90/3/5/2. The cleaved peptides were then extracted in ether and ethyl acetate and subsequently dissolved in water and lyophilized. Peptides were extensively dialyzed against water to remove the remaining cleavage products. Reverse phase HPLC analysis of crude peptides indicated one major peak in each profile. Hence, further purification was not warranted. Amino acid analysis of these peptides showed that the amino acid composition corresponded closely to theoretical.

Radioiodinations. Staphylococcal enterotoxins and synthetic peptides were radioiodinated using chloramine T as described elsewhere (Torres, B. A., N. D. Griggs, H. M. Johnson [1993] *Nature* 364:152–154). Briefly, ligands were labeled with 500 µCi of $Na^{125}I$ (15 mCi/µg, Amersham Corp., Arlington Heights, Ill.) in 25 µl of 0.5M potassium phosphate buffer, pH 7.4, and 10 µl of chloramine T (5 mg/ml) for 2 minutes. After neutralization of the reaction with 10 µl volume each of sodium bisulfite (10 mg/ml), potassium iodide (70 mg/ml), and BSA (20 mg/ml), and 15 µl of NaCl (4M), the preparation was sieved on a 5 ml Sepharose G-10 column. The two fractions with the highest radioactivity in the first eluted peak were pooled and used in the radiolabeled binding assays. The specific activities of the staphylococcal enterotoxins and synthetic peptides ranged from 70–120 µCi/µg and 30–40 µCi/µg, respectively.

Class II MHC binding studies. For binding studies using A20 cells, $1\times10^6$ A20 cells were incubated in 1.5 ml Eppendorf tubes with unlabeled competitors at room temperature for 45 minutes, followed by the addition of radiolabeled SEs or peptide. After an additional 45 minutes, one hundred microliters of reaction mixture was transferred to Ultrafree MC 5μ filter units to which 300 microliters of binding buffer had been added. Filter units were centrifuged at 14,000 rpm for two minutes and the radioactivity remaining in the filter units was quantified using a gamma counter.

For I-A peptide binding studies, synthetic I-A$\beta^b$(60–90) peptide (in 200 μl of 25 μg/ml solution in 0.1M bicarbonate/carbonate buffer, pH 9.6) was absorbed to the bottoms of 12 mm by 55 mm polystyrene tubes for 6 hours at 4 degrees Centigrade. The tubes were washed three times and the remaining active sites were blocked with PBS containing 0.5%BSA (2 ml/tube) overnight at 4 degrees Centigrade. After three washes, competitors (100 μl in PBS/BSA) were added for 4 hours at room temperature, followed by the addition of 5 nM (final concentration) of either $^{125}$I-SEA or $^{125}$I-MMTV ORF(76–119) [SEQ ID NO. 1] peptide in 100 μl volumes. The tubes were washed three times and the bound radioactivity was quantified using an gamma counter.

For binding studies using Raji cells, unlabeled competitors (SEs and peptides) in a 50 μl volume of PBS containing 1% BSA were added to 50 μl of 1×10$^5$ Raji cells in Eppendorf tubes to reach the final indicated concentrations. Competitors were incubated with cells at room temperature for 45 minutes, followed by the addition of radiolabeled SEs or peptide. After 45 minutes, the cells were washed three times, pelleted and the bottoms of the tubes were cut off. Radioactivity in the bottom of the tube was quantified using a gamma counter.

Cell proliferation assay. Peripheral blood donated by healthy volunteers was used as a source of human peripheral mononuclear cells (PMNC). PMNC were isolated from blood using Histapaque (Sigma Chemical Co., St. Louis, Mo.) density centrifugation at 1600 rpm for 20 minutes. Isolated PMNC were washed three times with RPMI 1640 medium (J. R. Scientific, Woodland, Calif.) to remove residual Histapaque. After the final wash, PMNC were resuspended in RPMI 1640 containing 5% fetal bovine serum (Intergen, Purchase, N.Y.). 2×10$^5$ PMNC/well and the purified NeF protein were plated in triplicate into the wells of 96-well microtiter plates in a final volume of 0.15 ml/well. Cultures were incubated at 37 degrees Centigrade in 5% CO$_2$. Cultures were pulsed with $^3$H-thymidine ($^3$H-TdR; 1 μCi/well; Amersham Corp., Arlington Heights, Ill.) 18 hours prior to harvest at the 48 and 96 hour time points. Cells were harvested using a PHD cell harvester (Cambridge, Mass.), washed with distilled water, and $^3$H-thymidine incorporation was determined as counts per minute (CPM) in a β-scintillation counter. The stimulation index was determined by using the following equation:

$$\text{Stimulation Index} = \frac{{}^3H\text{-}TdR \text{ incorporation by } NeF\text{-stimulated cells (in CPM)}}{{}^3H\text{-}TdR \text{ incorporation by unstimulated cells (in CPM)}}$$

Following are examples which illustrate procedures, including the best mode, for practicing the invention. These examples should not be construed as limiting. All percentages are by weight and all solvent mixture proportions are by volume unless otherwise noted.

EXAMPLE 1

Figure 3:
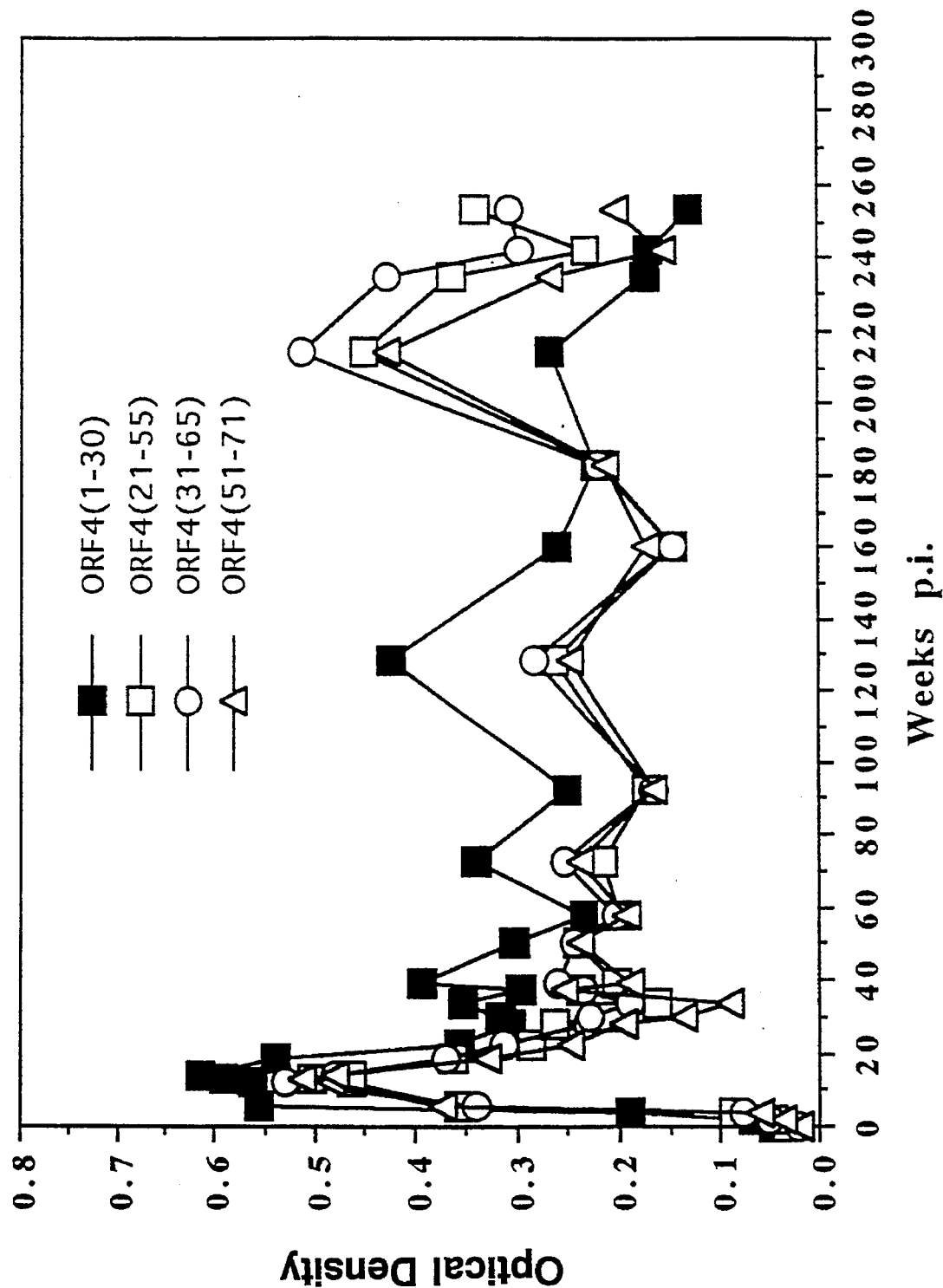
FIG. 3. ELISA reactivity of different FIV ORF4 peptides to pooled serum from FIV (Petaluma strain) infected cats drawn at different times post infection (pi).

Dose-Response Binding of MMTV ORF Peptides to Cells Expressing Class II MHC Molecules The dose-response binding of MMTV ORF peptides to a cell line expressing class II MHC molecules on its surface was assessed in a competitive inhibition protocol using $^{125}$I-SEA (FIG. 3). MMTV ORF(76–119) [SEQ ID NO. 1] peptide reduced $^{125}$I-SEA binding to A20 cells by 50% at a concentration of 20 μM. Unlabeled SEA was 20 times more effective a competitor than MMTV ORF(76–119) [SEQ ID NO. 1], which is consistent with the reported K$_d$ value for SEA binding to I-E$^d$. Therefore, MMTV ORF(76–119) [SEQ ID NO. 1] peptide competes with SEA for binding to A20 cells in a dose-dependent manner.

EXAMPLE 2

Binding of MMTV ORF(76–119) [SEQ ID NO. 1] Peptide to Class II MHC β-Chain Peptide The direct binding of $^{125}$-SEA and MMTV $^{125}$I-MMTV ORF(76–119) [SEQ ID NO. 1] peptide to I-A$\beta^b$(60–90) peptide was assessed by competitive radioimmunoassay. We have previously shown that SEA binds to the α-helical region of the class II MHC β-chain outside the antigen binding groove (Russel, J. K., C. H. Pontzer, H. M. Johnson [1991] *Proc. Natl. Acad. Sci. USA* 88:7228–7232). This region is encompassed by amino acid residues 60–90 of the β-chain. SEA and MMTV ORF(76–119) [SEQ ID NO. 1] both competed with $^{125}$I-SEA and $^{125}$I-MMTV ORF(76–119) [SEQ ID NO. 1] for binding to I-A$\beta^b$(60–90) peptide in a manner similar to the competition seen on whole cells. These results are consistent with the peptide binding data indicating class II MHC as the binding site of MMTV ORF(76–119) [SEQ ID NO. 1], and suggest that SEA and MMTV ORF(76–119) [SEQ ID NO. 1] bind to a similar region on the β-chain of the class II MHC molecule.

EXAMPLE 3

Detection of FIV ORF4 Peptides by Antibodies from FIV-vaccinated and FIV-Infected Cats Antisera from FIV-vaccinated and FIV-infected cats was assessed for the presence of antibodies reactive with the ORF4 peptides through an ELISA immunoassay. Vital-neutralizing serum obtained from virus-vaccinated and cell-vaccinated cats was reactive with FIV ORF4(1–30) [SEQ ID NO. 10] and FIV ORF4(21–55) [SEQ ID NO. 11] peptides. However, antisera reactivity was greatest with the FIV ORF4(1–30) [SEQ ID NO. 10] peptide. Pooled antisera drawn at various time intervals from FIV-infected cats reacted with all four of the ORF4 peptides. The peak reactivity was observed at 10 weeks post-infection, although all of the peptides except FIV ORF4(1–30) [SEQ ID NO. 10] showed a second peak of reactivity at about 220 weeks post-infection. This data suggests that the FIV superantigen protein corresponding to the ORF4 peptide fragments is expressed in vivo, since antisera from FIV-vaccinated and FIV-infected cats both react with the ORF4 peptides.

Immunoaffinity columns were prepared for each of the four ORF4 peptides using standard procedures. Partially purified antisera pooled from virus-vaccinated cats, which had previously been shown to protect cats from infection in passive immunization studies, was passed through an ORF4 peptide immunoaffinity column in order to purify any of the antibodies in the antisera that reacted with the particular peptide. Both the flow-through and the eluate from each column were tested for activity in a viral neutralization assay. High viral neutralization activity was observed in the eluate fraction from the FIV ORF4(1–30) [SEQ ID NO. 10] peptide column (FIG. 3). Fractions eluted from the other peptide columns did not contain viral neutralization activity, all of the viral neutralization activity being detected in the flow-through fraction of these columns.

This demonstrates a strong correlation between the presence of serum neutralizing antibodies and antibodies that are reactive with FIV ORF4 peptides. The viral neutralizing antibodies present in virus-vaccinated cats apparently recognize the N-terminal portion of the FIV ORF4(1–30) [SEQ ID NO. 10], since a 9 amino acid overlap occurs between FIV ORF4(1–30) [SEQ ID NO. 10] and FIV ORF4(21–55) [SEQ ID NO. 11].

EXAMPLE 4

Proliferative Response of Human Peripheral Mononuclear Cells to Recombinant HIV-1 NeF Protein The HIV-1 NeF protein was tested at various concentrations in a proliferation assay to determine its effects on human peripheral mononuclear cells (PMNC's). The NeF protein increased cell proliferation by almost six-fold over background when measured at 48 hours after initiation of the cell culture. However, this was followed by a rapid and sharp decline in proliferation to background levels by 96 hours, culminating in substantial cell death. Although the proliferative spike was greatest when NeF was used at a concentration of 300 ng/ml, the pattern of cell proliferation, followed by cell death, was observed at all concentrations of NeF tested (FIG. 5).

EXAMPLE 5

Dose-Response Binding of HIV-1 NeF(123–160) [SEQ ID NO. 18] Peptide to Cells Expressing Human Class II MHC Molecules The dose-response binding of HIV-1 NeF peptides to a human cell line expressing class II MHC molecules was assessed using a competitive inhibition protocol. HIV-1 NeF(123–160) [SEQ ID NO. 18] peptide reduced the binding of $^{125}$I-SEA to Raji cells by approximately 20% at a concentration of 30 μM, and approximately 40% at a concentration of 300 μM. HIV-1 NeF(1–38) [SEQ ID NO. 14] and HIV-1 NeF(31–65) [SEQ ID NO. 15] slightly reduced the binding of $^{125}$I-SEA to Raji cells at a peptide concentration of 300 μM.

It should be understood that the examples and embodiments described herein are for illustrative purposes only and that various modifications or changes in light thereof will be suggested to persons skilled in the art and are to be included within the spirit and purview of this application and the scope of the appended claims.

---

We claim:
1. A purified superantigen peptide, wherein said peptide consists of a peptide designated HIV-1 NeF(123–160) (SEQ ID NO. 18).

* * * * *

UNITED STATES PATENT AND TRADEMARK OFFICE
CERTIFICATE OF CORRECTION

PATENT NO. : 5,519,114

DATED : May 21, 1996

INVENTOR(S) : Howard M. Johnson; Barbara A. Torres; Janet K. Yamamoto

It is certified that error appears in the above-indentified patent and that said Letters Patent is hereby corrected as shown below:

Column 3: Line 45: "*I Immunol.*" should read --*J. Immunol.*--; Line 50: "*I Exp.*" should read --*J. Exp.*--; Line 57: "beating" should read --bearing--.

Column 4: Line 18: "Hashim, .A.A." should read --Hashim, A.A.--.

Column 6: Line 22: "FW" should read --FIV--.

Column 9: Line 10: "fines" should read --lines--.

Column 13: Line 57: "an" should read --art--.

Column 14: Line 29: "HW-1" should read --HIV-1--.

Column 16: Line 40: "Vital-neutralizing" should read --Viral-neutralizing--.

Column 27: Line 47, Claim 1: "(SEQ           " should read --(SEQ ID NO. 18).--.

Column 27: Line 45: Claim 1: delete "ID No. 18)."

Signed and Sealed this

Twenty-ninth Day of October 1996

Attest:

BRUCE LEHMAN

Attesting Officer       Commissioner of Patents and Trademarks